United States Patent
Uematsu et al.

(10) Patent No.: US 12,317,889 B2
(45) Date of Patent: Jun. 3, 2025

(54) STORAGE CONTAINER

(71) Applicant: Nagasaki University, Nagasaki (JP)

(72) Inventors: Masafumi Uematsu, Nagasaki (JP);
Takashi Kitaoka, Nagasaki (JP)

(73) Assignee: Nagasaki University, Nagasaki (JP)

( * ) Notice: Subject to any disclaimer, the term of this patent is extended or adjusted under 35 U.S.C. 154(b) by 771 days.

(21) Appl. No.: 17/681,432

(22) PCT Filed: Aug. 20, 2020

(86) PCT No.: PCT/JP2020/031428
§ 371 (c)(1),
(2) Date: Feb. 25, 2022

(87) PCT Pub. No.: WO2021/039575
PCT Pub. Date: Mar. 4, 2021

(65) Prior Publication Data
US 2022/0174942 A1     Jun. 9, 2022

(30) Foreign Application Priority Data

Aug. 29, 2019 (JP) .................. 2019-156415

(51) Int. Cl.
*A01N 1/10* (2025.01)
*A01N 1/146* (2025.01)
(Continued)

(52) U.S. Cl.
CPC ............ *A01N 1/146* (2025.01); *A61F 2/0095* (2013.01); *A61F 2/142* (2013.01)

(58) Field of Classification Search
CPC . A01N 1/10; A01N 1/14; A01N 1/146; A01N 1/148
See application file for complete search history.

(56) References Cited

U.S. PATENT DOCUMENTS 4,844,242 A    7/1989  Chen et al.
5,789,240 A *  8/1998  Abdulrazik ............ G01N 33/15
                                              435/284.1
(Continued)

FOREIGN PATENT DOCUMENTS

JP    2008-518034    5/2008
JP    2010-528983    8/2010
JP    2016-512492    4/2016

OTHER PUBLICATIONS

Means, Teresa L. et al., Viability of Human Corneal Endothelium Following Optisol-GS Storage, Arch. Ophthalmol. 113, 805-809(1995).

(Continued)

*Primary Examiner* — Jonathan M Hurst
(74) *Attorney, Agent, or Firm* — Chernoff, Vilhauer, McClung & Stenzel, LLP

(57) ABSTRACT

A storage container for storing a cornea specimen in which an endothelium and an epithelium of a cornea can be immersed and stored in different storage solutions. The storage container 1A has a specimen-supporting portion 3A containing a first cornea exposure portion 31*a* and a second cornea exposure portion 31*b* that expose a cornea part 101, the specimen-supporting portion supporting a scleral rim 102 at an outer circumferential side of the first and second cornea exposure portions 31*a*, 31*b*; a first chamber 20*a*; and a second chamber 20*b*, where the second chamber is divided from the first chamber 20*a* by the specimen-supporting portion 3A, and the second chamber containing a second storage solution 60*b* that differs from the first storage solution 60*a*, wherein the storage container is configured to prevent the first and second storage solutions 60*a*, 60*b* from being circulated between the first and second chambers 20*a*, 20*b*.

5 Claims, 5 Drawing Sheets

(51) Int. Cl.
   *A61F 2/00*      (2006.01)
   *A61F 2/14*      (2006.01)

(56)             References Cited

U.S. PATENT DOCUMENTS

| | | | | |
|---|---|---|---|---|
| 6,256,089 | B1* | 7/2001 | Baker | G01N 21/59 |
| | | | | 356/73 |
| 7,147,826 | B2* | 12/2006 | Haywood | A01N 1/146 |
| | | | | 435/288.1 |
| 9,371,508 | B2* | 6/2016 | Angeloni Suter | C12M 23/00 |
| 2005/0136391 | A1* | 6/2005 | Steinhardt | A01N 1/126 |
| | | | | 435/375 |
| 2008/0294149 | A1* | 11/2008 | Krolman | A01N 1/146 |
| | | | | 606/1 |
| 2016/0029618 | A1* | 2/2016 | Gain | A01N 1/146 |
| | | | | 435/284.1 |
| 2018/0206482 | A1* | 7/2018 | Zhang | A01N 1/146 |

OTHER PUBLICATIONS

Katori, Ryosuke et al, Ebselen Preserves Tissue-Engineered Cell Sheets and their Stem Cells in Hypothermic Conditions, Scientific Reports 6:38987, Dec. 14, 2016.

* cited by examiner

[FIG.1]
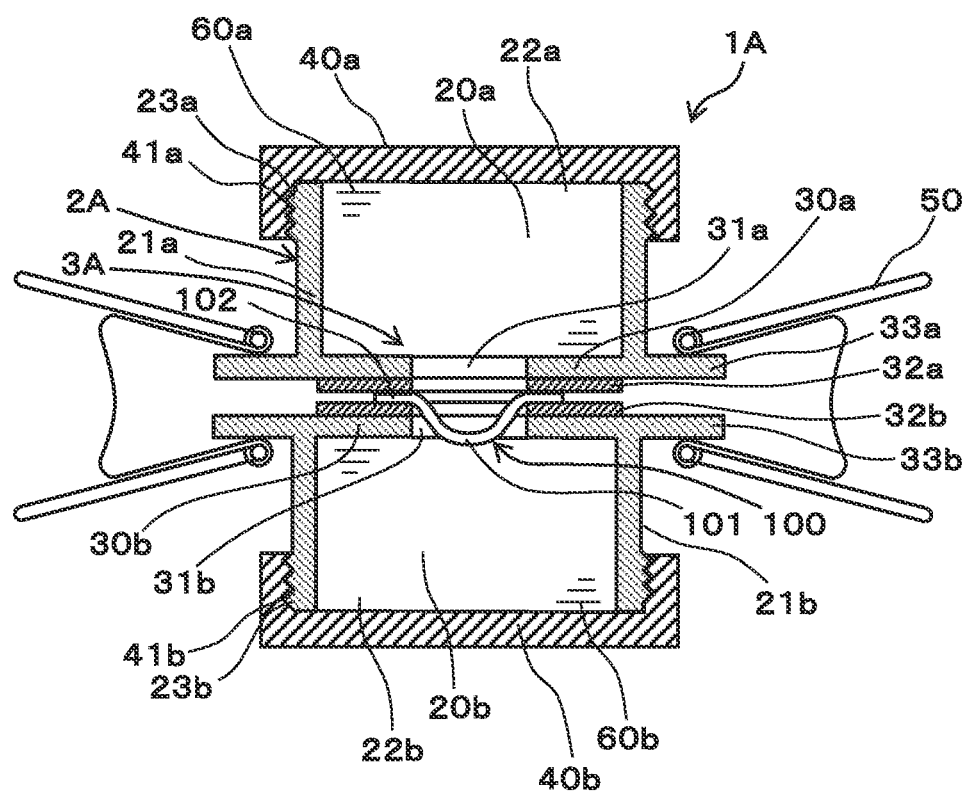

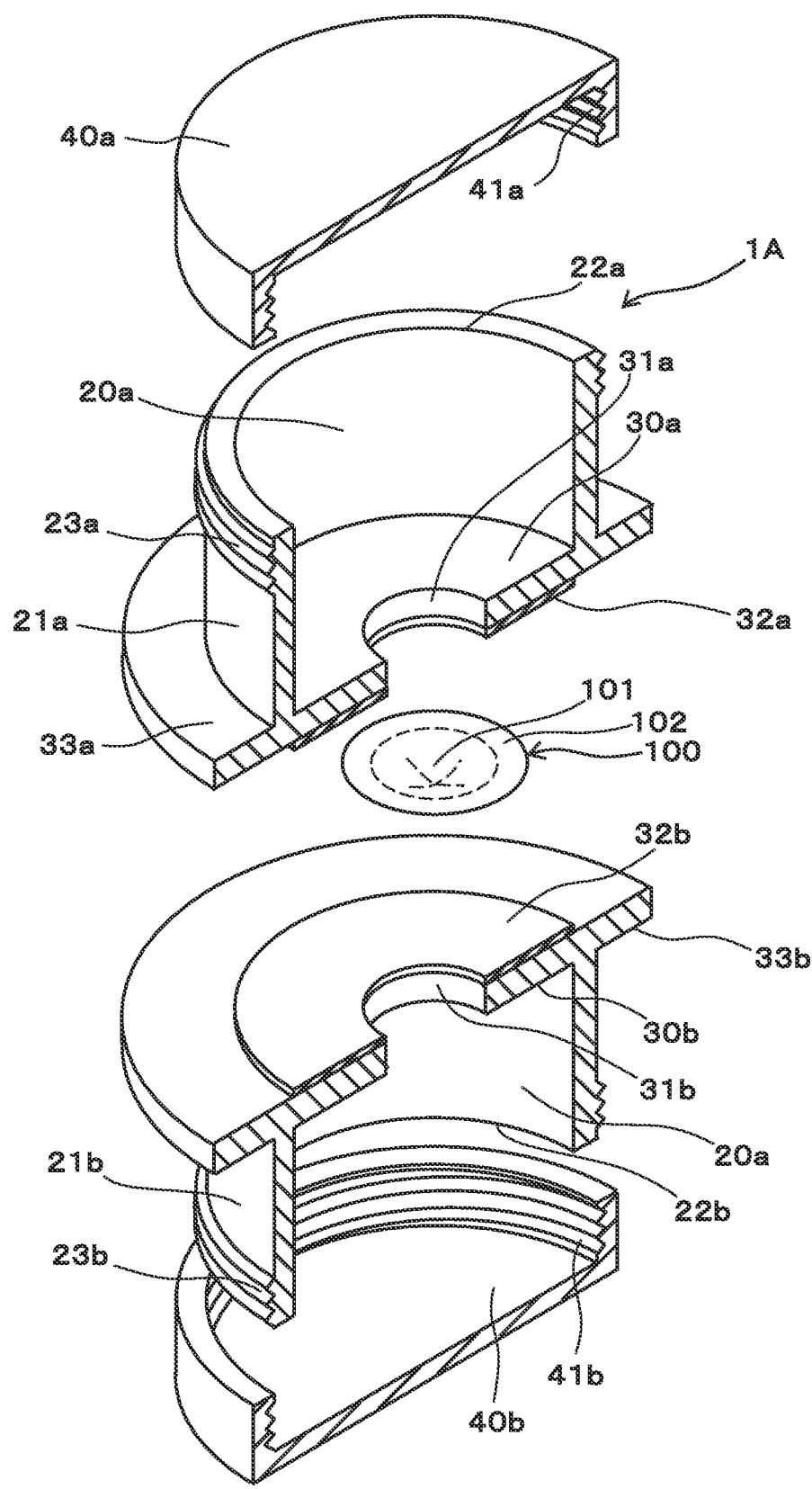
[FIG.2]

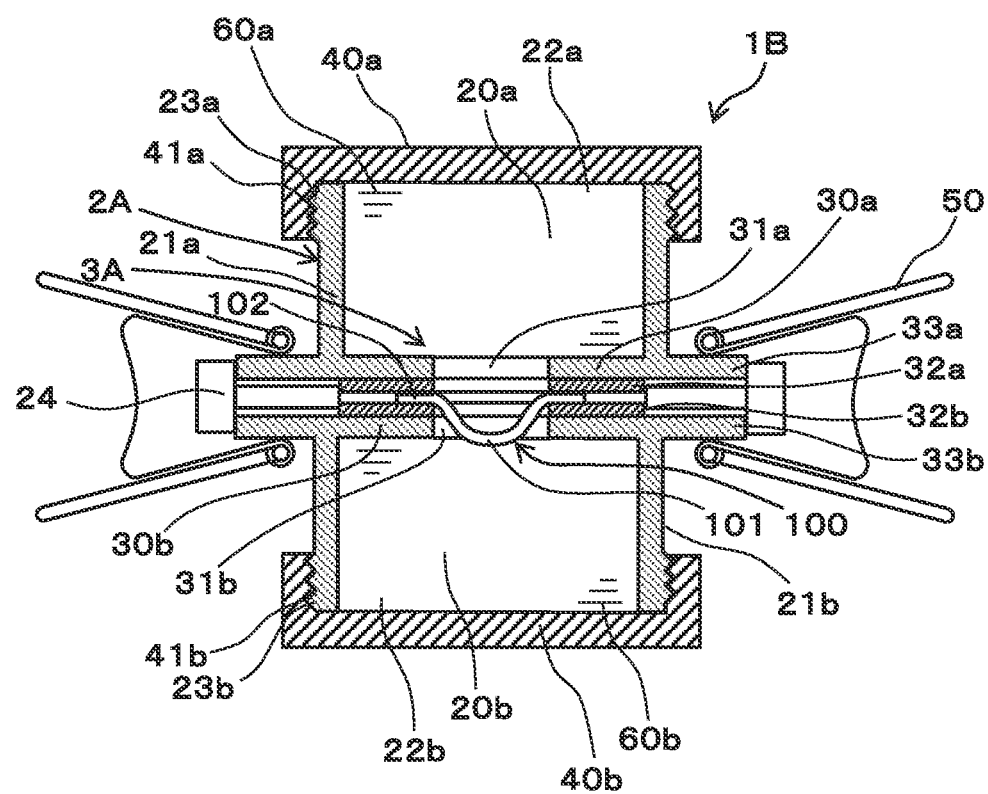
[FIG.3]

[FIG.4]
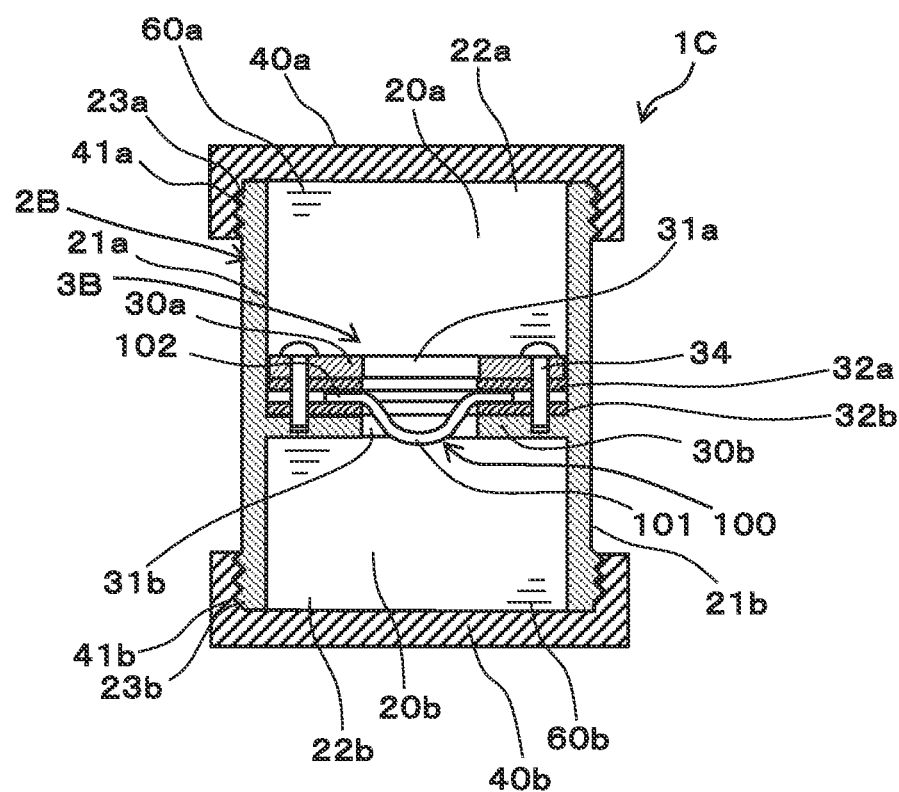

[FIG.5]
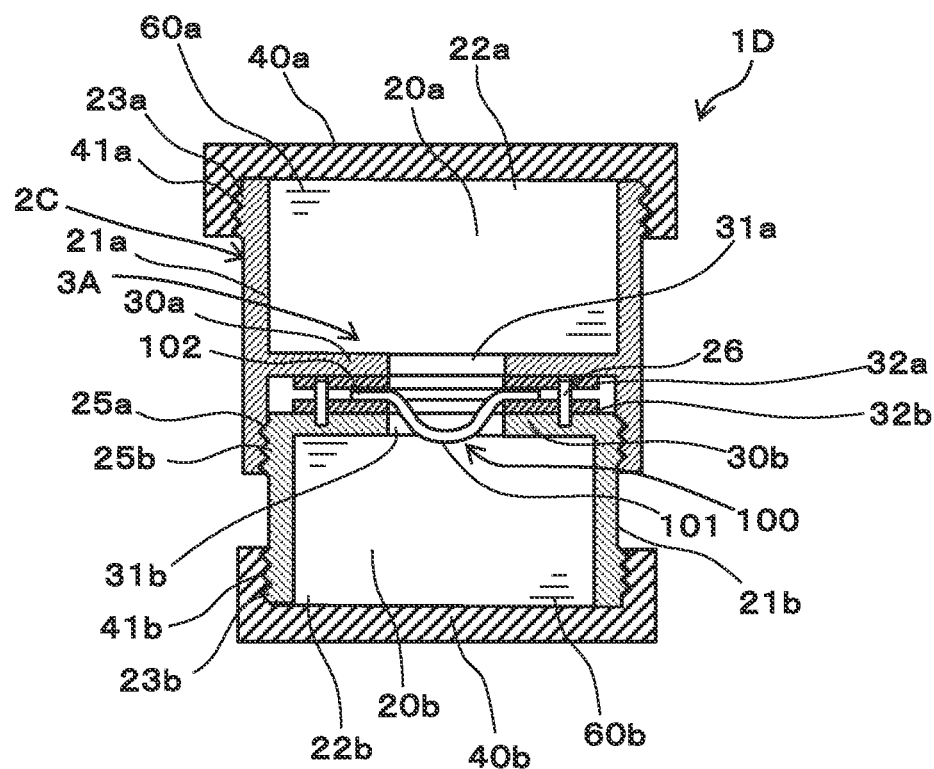

STORAGE CONTAINER

TECHNICAL FIELD

The present invention relates to a storage container for use and transplantation of a cornea of a human being and that of an animal.

BACKGROUND ART

The cornea, which is applied to the transplantation, has been cut with a ring-shaped scleral rim being left and has been generally stored in a storage container such as a simple glass bottle or a plastic case in which the cut piece is not bound, to be immersed in any filled storage solution.

A patent document 1 discloses a structure for clamping the scleral rim with a receiving surface and a mating surface to secure the cut corneal piece in the storage container. In addition, a patent document 2 discloses that a pressure gradient is created from an endothelium side of the cornea to an epithelium side thereof and discloses a structure for circulating the preservation medium to both of the endothelium side and the epithelium side. Namely, it discloses the structure containing an intermediate component (2) having a central hole which corresponds to a diameter of a cornea (3a) of a cornea specimen (3) and a circumferential groove for receiving sclera central (3b); an endothelium chamber (18) having orifices (7a and 7b as well as 11a and 11b) which are connected to the means for the circulation of the preservation medium and the creation of the pressure gradient; and an epithelium chamber (19).

In the above-mentioned past storage containers, the currently most used storage solution in general is Optisol GS (registered trademark) for sale on the market and a nonpatent document 1 reports that it is particularly suitable for storage of the endothelium of the cornea. In the meantime, a nonpatent document 2 reports that Optisol GS (registered trademark) is not suitable for storage of the epithelium of the cornea but ebselen solution is suitable therefor. Since the endothelium and epithelium of the cornea are different from each other in their tissue structure, it is desirable to immerse them in any different storage solutions but in the above-mentioned past storage containers, only one storage solution can be used.

PRIOR ART DOCUMENTS

Patent Documents

Patent document 1: Japanese Patent Kohyo Publication No. 2008-518034; and
Patent document 2: Japanese Patent Kohyo Publication No. 2016-512492.

Nonpatent Documents

Nonpatent document 1: Arch. Ophthalmol. 113, 805-809 (1995) "Viability of human corneal endothelium following Optisol-GS storage; and
Nonpatent document 2: Scientific Reports 6:38987 Dec. 14, 2016 "Ebselen Preserves Tissue-Engineered Cell Sheets and their Stem Cells in Hypothermic Conditions".

SUMMARY OF THE INVENTION

Problems to be Solved by the Invention

An object of this invention is to present a storage container for storing a cornea specimen containing an entire cornea part which includes an endothelium and an epithelium of the cornea and a scleral rim whereby it is possible to store the cornea specimen with the endothelium of the cornea and the epithelium of the cornea being immersed in different storage solutions.

Means for Solving the Problems

To solve the above-mentioned problem, this invention relates to a storage container for storing a cornea specimen containing a cornea part and a scleral rim, the storage container including a specimen-supporting portion which contains a cornea exposure portion that exposes the cornea part, the specimen-supporting portion supporting the scleral rim at an outer circumferential side of the cornea exposure portion; a first chamber to which an endothelium side of the cornea part in the cornea specimen is exposed, the scleral rim of the cornea specimen being supported by the specimen-supporting portion, and the first chamber containing a first storage solution; and a second chamber to which an epithelium side of the cornea part in the cornea specimen is exposed, the scleral rim of the cornea specimen being supported by the specimen-supporting portion, the second chamber being divided from the first chamber by the specimen-supporting portion, and the second chamber containing a second storage solution that differs from the first storage solution, wherein the storage container is configured to prevent the first and second storage solutions from being circulated between the first and second chambers.

Advantage of the Invention

By this invention, the endothelium of the cornea can be immersed into the first storage solution that is suitable for the storage of the endothelium thereof and the epithelium of the cornea can be immersed into the second storage solution that is suitable for the storage of the epithelium thereof. This prevents the first and second storage solutions from being mixed. Accordingly, it is possible to store a cornea specimen in a storage container having a simple configuration.

BRIEF DESCRIPTION OF THE DRAWINGS

FIG. 1 is a cross sectional side view showing an example of a storage container of a first embodiment;
FIG. 2 is a sectional perspective view showing the example of the storage container of the first embodiment;
FIG. 3 is a cross sectional side view showing an example of a storage container of a second embodiment;
FIG. 4 is a cross sectional side view showing an example of a storage container of a third embodiment; and
FIG. 5 is a cross sectional side view showing an example of a storage container of a fourth embodiment.

EMBODIMENTS FOR CARRYING OUT THE INVENTION

The following will describe embodiments of a storage container according to the invention.

Configuration Example of a Storage Container of Embodiments

FIG. 1 is a cross sectional side view showing an example of a storage container of a first embodiment and FIG. 2 is a sectional perspective view showing the example of the storage container of the first embodiment.

A storage container 1A according to the first embodiment is a storage container for storing a cornea specimen 100 containing a cornea part 101 and a scleral rim 102, which is provided with a main body portion 2A and a specimen-supporting portion 3A for supporting the cornea specimen 100.

The main body portion 2A is configured to have a tubular shape such as a cylindrical shape and the specimen-supporting portion 3A is provided at almost center of an internal wall of the tube along an axis direction thereof. The main body portion 2A is provided with a first chamber 20a into which a first storage solution 60a is poured and a second chamber 20b into which a second storage solution 60b is poured, the second chamber being divided from the first chamber 20a by the specimen-supporting portion 3A.

The main body portion 2A is configured to be composed of two parts, the first and second main body portions 21a and 21b. The first main body portion 21a is provided with the first chamber 20a and a first holding portion 30a constituting the specimen-supporting portion 3A. In addition, the second main body portion 21b is provided with the second chamber 20b and a second holding portion 30b constituting the specimen-supporting portion 3A.

When the first chamber 20a is placed upward and the second chamber 20b is placed downward, in the main body portion 2A, the first holding member 30a forms a bottom surface of the first chamber 20a and the second holding member 30b forms a top surface of the second chamber 20b.

The first holding portion 30a has an opening, for example, circular opening having a diameter that is larger than a diameter of the cornea part 101 and smaller than a diameter of the scleral rim 102, on a center of a radial direction, which forms a first cornea exposure portion 31a. The first holding portion 30a has a flat shape on an outer circumference of the first cornea exposure portion 31a and comes into contact with the endothelium side of the scleral rim 102 of the cornea specimen 100. The first holding portion 30a is provided with a sealing member 32a on the outer circumference of the first cornea exposure portion 31a which the endothelium side of the scleral rim 102 contacts.

The second holding portion 30b also has an opening, for example, circular opening having a diameter that is larger than a diameter of the cornea part 101 and smaller than a diameter of the scleral rim 102, on a center of a radial direction, which forms a second cornea exposure portion 31b. The second holding portion 30b has a flat shape on an outer circumference of the second cornea exposure portion 31b and comes into contact with the epithelium side of the scleral rim 102 of the cornea specimen 100. The second holding portion 30b is provided with a sealing member 32b on the outer circumference of the second cornea exposure portion 31b which the epithelium side of the scleral rim 102 contacts. Additionally, there may be a case where any sealing members 32a, 32b may be not provided if any flatness is secured on the scleral rim 102.

The specimen-supporting portion 3A is provided with a first pressure-receiving portion 33a constituting a pressure-applying portion on an outer circumference of the first holding portion 30a and a second pressure-receiving portion 33b constituting the pressure-applying portion on an outer circumference of the second holding portion 30b. The first pressure-receiving portion 33a is configured so as to project outward from an outer circumference of the first main body portion 21a and the second pressure-receiving portion 33b is configured so as to project outward from an outer circumference of the second main body portion 21b.

The specimen-supporting portion 3A supports the sclera rim 102 of the cornea specimen 100 between the first holding portion 30a and the second holding portion 30b on an outer circumferential side of each of the first and second cornea exposure portion 31a, 31b. In addition, in the specimen-supporting portion 3A, the cornea part 101 of the cornea specimen 100 is exposed to the first cornea exposure portion 31a and the second cornea exposure portion 31b.

In the first chamber 20a, the endothelium side of the cornea part 101 is exposed to the first cornea exposure portion 31a of the first holding portion 30a. In the second chamber 20b, the epithelium side of the cornea part 101 is also exposed to the second cornea exposure portion 31b of the second holding portion 30b.

Thereby, when supporting the cornea specimen 100 by the specimen-supporting portion 3A, the first chamber 20a and the second chamber 20b are divided by the specimen-supporting portion 3A and the cornea specimen, in the main body portion 2A, with air-tightness and water-tightness thereof being kept.

In the first chamber 20a, a first opening 22a is formed on an opposite side of the first holding portion 30a and the first storage solution 60a is poured from the first opening 22a. The first chamber 20a is provided with a first cap 40a on the first opening 22a.

The first cap 40a is tightened on the first main body portion 21a by screwing a male screw portion 23a formed on an outer circumference surface of the first main body portion 21a with a female screw portion 41a formed on an inner circumference surface of the first cap 40a to seal the first opening 22a with its air-tightness and water-tightness being kept.

In the second chamber 20b, a second opening 22b is formed on an opposite side of the second holding portion 30b and the second storage solution 60b is poured from the second opening 22b. The second chamber 20b is provided with a second cap 40b on the second opening 22b.

The second cap 40b is tightened on the second main body portion 21b by screwing a male screw portion 23b formed on an outer circumference surface of the second main body portion 21b with a female screw portion 41b formed on an inner circumference surface of the second cap 40b to seal the second opening 22b with its air-tightness and water-tightness being kept.

The main body portion 2A is configured so that when the first opening 22a is sealed by the first cap 40a and the second opening 22b is sealed by the second cap 40b, the first storage solution 60a poured into the first chamber 20a and the second storage solution 60b poured into the second chamber 20b cannot be circulated between the first chamber 20a and the second chamber 20b.

The following will describe how to use the storage container 1A. The cornea part 101 of the cornea specimen 100 is positioned on the second cornea exposure portion 31b and the sclera rim 102 is mounted on the second holding portion 30b according to the endothelium exposure direction.

Next, the cornea part 101 is positioned on the first cornea exposure portion 31a and the first holding portion 30a is mounted on the sclera rim 102 according to the epithelium exposure direction.

Plural clips 50 constituting the pressure-applying portion then clip the first pressure-receiving portion 33a and the pressure-receiving portion 33b so as to be a closely attached condition. This allows the first holding portion 30a and the second holding portion 30b to be pressurized on an axis direction.

The first storage solution 60a is then poured into the first chamber 20a and the first opening 22a is sealed by the first cap 40a. After the main body portion 2A is reversed, the second storage solution 60b is then poured into the second chamber 20b and the second opening 22b is sealed by the second cap 40b.

Thereby, in the storage container 1A, the endothelium of the cornea part 101 can be immersed into the first storage solution 60a such as Optisol GS (registered trade mark), which is suitable for storage of the endothelium, and the epithelium of the cornea part 101 can be immersed into the second storage solution 60b such as ebselen solution, which is suitable for storage of the epithelium. This prevents the first and second storage solutions 60a, 60b from being mixed. Accordingly, it is possible to store the cornea specimen 100 by the storage container 1A with a simple configuration.

Variations of the Storage Container According to Embodiments

FIG. 3 is a cross sectional side view showing an example of the storage container of a second embodiment. In the following description of each embodiment, like codes are applied to members having the same functions as those of members in the storage container 1A of the first embodiment, the detailed explanation of which will be omitted.

A storage container 1B according to the second embodiment is provided with positioning members 24 for matching the positions of the first and second main body portions 21a, 21b. The positioning members 24 match the positions of the first and second main body portions 21a, 21b on a radial direction thereof, namely, match the positions of the first and second cornea exposure portions 31a, 31b on a radial direction thereof, by contacting an outer circumference of the first pressure-receiving portion 33a and an outer circumference of the second pressure-receiving portion 33b.

FIG. 4 is a cross sectional side view showing an example of a storage container of a third embodiment. A storage container 1C according to the third embodiment has a main body portion 2B integrally configured as one body. In the specimen-supporting portion 3B, the second holding portion 30b is integrally configured with the main body portion 2B but the first holding portion 30a is separately configured with the main body portion 2B. The first holding portion 30a is attached to the second holding portion 30b by plural screws 34 constituting the pressure-applying portion.

FIG. 5 is a cross sectional side view showing an example of a storage container of a fourth embodiment. In a storage container 1D according to the fourth embodiment, the first main body portion 21a and the second main body portion 21b are tightened by screwing a female screw portion 25a constituting the pressure-applying portion, which is formed on an inner circumference surface of the first main body portion 21a, with a male screw portion 25b constituting the pressure-applying portion, which is formed on an outer circumference surface of the second main body portion 21b, to configure the main body portion 2C. In addition, locking members 26 such as pins, each being inserted to pass through the sealing members 32a, 32b but not to pass through the second main body 21b, are provided to prevent the sealing members 32a, 32b and the cornea specimen 100 from being rotated when screwing the first main body portion 21a with the second main body portion 21b.

DESCRIPTION OF CODES 1A, 1B, 1C, 1D . . . Storage Container
2A . . . Main Body Portion
20a . . . First Chamber
20b . . . Second Chamber
21a . . . First Main Body Portion
21b . . . Second Main Body Portion
22a . . . First Opening
22b . . . Second Opening
23a, 23b . . . Male Screw
24 . . . Positioning Members
25a . . . Female Screw
25b . . . Male Screw
26 . . . Locking Members
3A . . . Specimen-Supporting Portion
30a . . . First Holding Portion
30b . . . Second Holding Portion
31a . . . First Cornea Exposure Portion
31b . . . Second Cornea Exposure Portion
32a, 32b . . . Sealing Member
33a . . . First Pressure-Receiving Portion
33b . . . Second Pressure-Receiving Portion
34 . . . Screws
40a . . . First Cap
40b . . . Second Cap
41a, 41b . . . Female Screw
50 . . . Clips
60a . . . First Storage Solution
60b . . . Second Storage Solution

The invention claimed is:

1. A storage container for storing a cornea specimen containing a cornea part and a scleral rim, the storage container comprising:
a specimen-supporting portion which contains a cornea exposure portion that exposes the cornea part, the specimen-supporting portion supporting the scleral rim at an outer circumferential side of the cornea exposure portion;
a first chamber to which an endothelium side of the cornea part in the cornea specimen is exposed, the scleral rim of the cornea specimen being supported by the specimen-supporting portion, and the first chamber containing a first storage solution; and
a second chamber to which an epithelium side of the cornea part in the cornea specimen is exposed, the scleral rim of the cornea specimen being supported by the specimen-supporting portion, the second chamber being divided from the first chamber by the specimen-supporting portion, and the second chamber containing a second storage solution that differs from the first storage solution, wherein the storage container is configured to prevent the first and second storage solutions from being circulated between the first and second chambers.

2. The storage container according to claim 1 wherein the specimen-supporting portion contains first and second holding portions for cramping the scleral rim and a pressure-applying portion for applying pressure on the first and second holding portions along an axis direction.

3. The storage container according to claim 2 wherein the storage container comprises:
a main body portion including the first and second chambers which are divided from each other by the specimen-supporting portion;
a first openable cap with which a first opening facing the first chamber of the main body portion is sealed; and
a second openable cap with which a second opening facing the second chamber of the main body portion is sealed.

4. The storage container according to claim 3 wherein the main body portion includes:
- a first main body portion containing the first chamber and a second main body portion containing the second chamber, and the specimen-supporting portion includes:
- the first holding portion on the first main body portion and the second holding portion on the second main body portion.

5. The storage container according to claim 2 wherein the cornea exposure portion contains a first cornea exposure portion for exposing the endothelium side of the cornea part on the first holding portion and a second cornea exposure portion for exposing the epithelium side of the cornea part on the second holding portion.

* * * * *